United States Patent [19]

Miller

[11] 4,369,786
[45] Jan. 25, 1983

[54] REFASTENABLE ADHESIVE CLOSURE FOR DISPOSABLE DIAPERS OR BRIEFS

[75] Inventor: Ezra D. Miller, Painesville, Ohio

[73] Assignee: Avery International Corporation, Pasadena, Calif.

[21] Appl. No.: 228,307

[22] Filed: Jan. 26, 1981

[51] Int. Cl.³ .............................................. A41B 13/02
[52] U.S. Cl. ............................. 604/390; 128/DIG. 30
[58] Field of Search ............... 128/284, 287, DIG. 30; 428/40, 261

[56] References Cited

U.S. PATENT DOCUMENTS

| 4,010,754 | 3/1977 | Pieniak | 128/DIG. 30 |
| 4,111,205 | 9/1978 | Nemeth | 128/287 |
| 4,186,744 | 2/1981 | Ness | 128/287 |
| 4,209,016 | 6/1980 | Schaar | 128/287 |
| 4,299,223 | 11/1981 | Cronkrite | 128/287 |

Primary Examiner—C. Fred Rosenbaum
Attorney, Agent, or Firm—Pearne, Gordon, Sessions, McCoy & Granger

[57] ABSTRACT

A refastenable diaper tab of Y-configuration is provided by forming the user end of the principal tab substrate as a pair of half-tab parts which can be separately deployed, fastened, and unfastened.

2 Claims, 6 Drawing Figures

REFASTENABLE ADHESIVE CLOSURE FOR DISPOSABLE DIAPERS OR BRIEFS

This invention relates to tabs for disposable diapers or geriatric briefs or the like.

In the manufacture of disposable diapers, it is typical practice for the diaper manufacturer to provide diaper tabs fixed to the diaper proper. Each tab is permanently attached at its "factory end" to the diaper and its other "user end" is then later fastened to another part of the diaper by the parent or other user who purchases and applies the diaper. The user end is provided with a pressure-sensitive adhesive which is suitably protected prior to use. The user manipulates the user end to expose the adhesive and then presses the user end and its exposed adhesive against a receiving portion of the diaper to accomplish the original fastening of the diaper.

One desirable feature of a diaper tab is that it have a "Y-configuration", i.e., the shape of a Y whose two arms and stem all bear adhesive, the arms being adapted to be fastened by the diaper manufacturer to both sides of one portion of a diaper adjacent an edge, and the stem being adapted to be fastened to another part of the diaper by the user. Tabs of Y-configuration provide increased or double strength where it is most needed-at the diaper-to-tab connection which receives the strain when the person applying the diaper pulls on the tab to draw the diaper tight before closing it. The present invention relates to a tab of this type.

A parent or user will frequently wish to temporarily open a diaper in order to inspect it and then continue its use if it is still clean and dry, or in order to adjust it. For these purposes, the diaper tab must be capable of unfastening and refastening, and there is therefore a demand for diaper tabs with this refastening capability.

It is known to provide tabs of Y-configuration with refastening capability. Ib Richman U.S. Pat. No. 4,020,842 of common assignee, three substrates are provided to achieve both a Y-configuration and refastenability. In Nemeth U.S. Pat. No. 4,178,933 of common assignee, a pair of release coats included within the tab construction provide for "extractive transfer" of adhesive and provide for both refastenability and Y-configuration utilizing only two substrates. However, even the "extractive transfer" arrangement is relatively complex as compared to the present invention. The present invention uses extremely simple means to provide a refastenable tab of Y-configuration and requires only that present manufacture of non-reclosable tabs of Y-configuration be modified by the addition of a cut, and preferably a change in overall tab width, without the modification or addition of any coatings or coating steps. The refastenable tab can be simply fashioned from a tab stock construction made up of initially flat but flexible substrate material and suitable to be formed in long passes along the machine direction of a coating and laminating line and to be rolled up for storage and shipment and unrolled for use by diaper manufacturers, and fabricatable for storage and shipment completely by web coating and web-to-web laminating operations and without the necessity for folding or machine direction slitting operations, and suitable for high speed dispensing or automatic equipment.

In the drawings, the thicknesses of the webs and coatings are greatly exaggerated.

Figure 1:
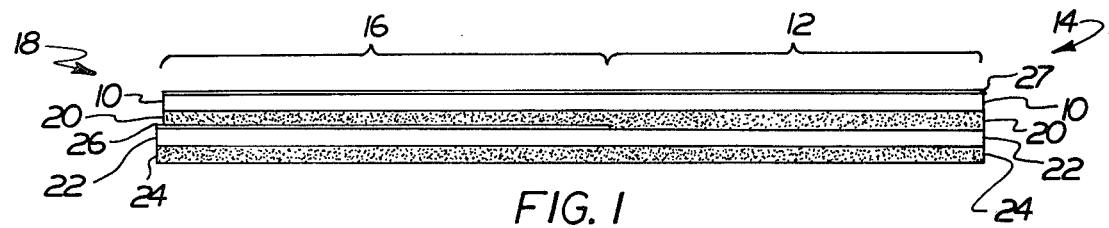
FIG. 1 is a schematic transverse elevation of diaper tab stock constructed according to the invention and then cut transversely to machine direction (machine direction being directly into the surface of the page) into an individual diaper tab laminate.

As seen in FIG. 1, the web construction comprises a first or principal substrate 10 extending, transversely to machine direction, along first and second length portions 12 and 16, respectively. The first length portion 12 corresponds to the factory end 14 and the second length portion 16 corresponds to the user end 18. The first substrate 10 bears first substrate adhesive 20 on its underside.

A second substrate 22 also extends along the first and second length portions. The second substrate bears the second substrate adhesive 24 on its underside. The second substrate adhesive extends along the first and second length portions, as shown.

Release means 26 is provided for the first substrate adhesive 20. The release means 26 is located below the first substrate adhesive at the second length portion 16, as seen in FIG. 1. The first length portion 12 is substantially free of the release means 26. The release means 26 is on the top side of the second substrate 22.

In order that the stock shown in FIG. 1 may be self-wound, additional release means 27 may be provided on the top side of the first or principal substrate 10.

Figure 3:
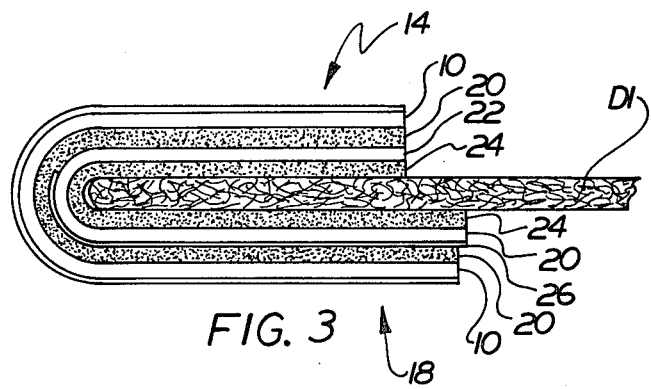
FIG. 3 is a view of the laminate shown in FIG. 1 as folded and fastened at one edge of one portion of a diaper by the diaper manufacturer.

The construction in the form described and shown in FIG. 1 can be supplied to a diaper manufacturer as a self-wound roll of diaper tab stock. The diaper manufacturer cuts the roll of diaper tab stock transversely to form a succession of individual tabs and folds the first and second length portions 12 and 16 of each successive tab around a first portion D1 of a diaper, as seen in FIG. 3, applying the second substrate adhesive 24 to the diaper to anchor the tab in mounted condition. All this is known practice.

Figure 2:
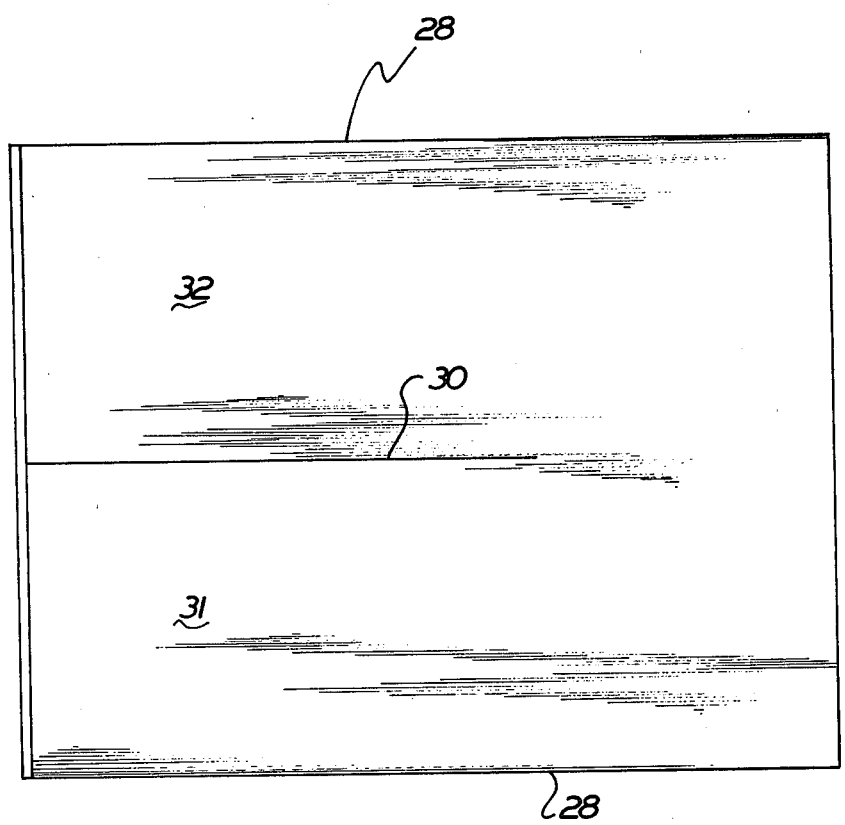
FIG. 2 is a plan view of the diaper tab seen in FIG. 1.

According to the present invention, the diaper tab is cut to a double width, or at least to a substantially increased width as compared with prior practice, and is provided with an intermediate cut 30 (FIG. 2) within the tab body and extending generally intermediate the two lateral tab sides 28,28, and generally parallel thereto. The intermediate cut 30 extends at least through the second length portion 16 (FIG. 1) of the first or principal substrate 10 to form two side-by-side half-tab parts 31, 32 (FIG. 2) of the first or principal substrate 10. Although the cut 30 is shown in FIG. 2 as extending only through the principal or first substrate 20 and not through the second substrate 22, the cut 30 may also be extended through the latter, and it may also be extended back into the first length portion 12. However, with the cut 30 extended only into the first or principal substrate as shown, greatest stability of the overall construction is maintained during handling of tab stock and formation and application of individual tabs by the diaper manufacturer, since such restriction of the extent of the cut 30 causes the half-tab parts 31, 32 to remain temporarily tied together even at their outer ends by the uncut second substrate 22.

Although the location of the cut 30 may be properly described with reference to the two lateral sides 28,28 of the individual tab illustrated, it should be understood that the cut 30 may be formed prior to the cuts which form the sides 28,28. Thus, the manufacturer of the tab stock may form the cut 30 as one of a series of similar parallel cuts in the tab stock, such cuts being of course transverse to machine direction. The diaper manufacturer may then at a later time form the tab as one of a series of similar tabs by performing the cuts which sever the tab stock, transversely to machine direction, to form the tab sides 28,28. Rather than being formed simultaneously, the two sides 28 of the individual tab may be, and generally will be, formed sequentially by successive severing operations performed on the label stock. Of course, when forming individual tabs by severing short lengths of tab stock, the diaper manufacturer maintains proper register between the pre-existing cuts 30 and the severing cuts which form the sides 28,28.

Figure 4:
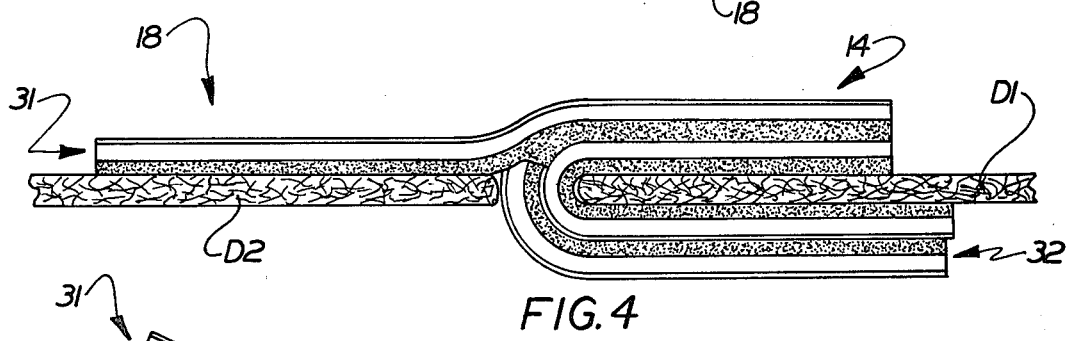
FIG. 4 is a view of the same laminate, with one half-tab part now unfolded to join the tab to another portion of the diaper.
Figure 5:
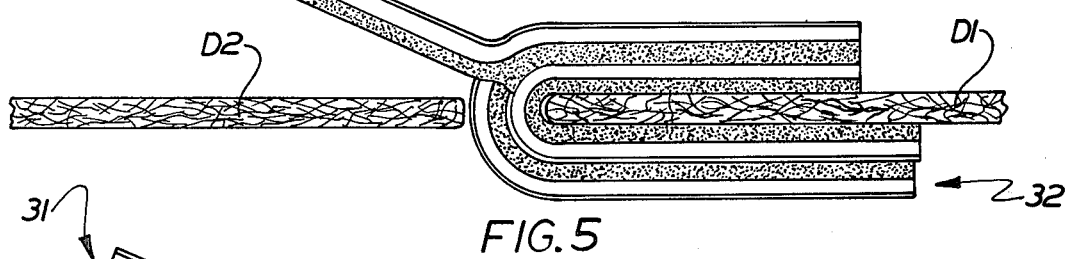
FIG. 5 is a view similar to FIG. 4 showing the parts at the time the diaper tab is unfastened following original fastening.
Figure 6:
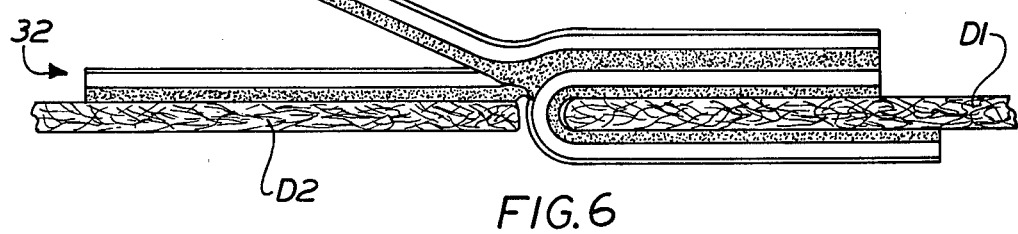
FIG. 6 is a view of the same tab with the other half-tab part now unfolded to rejoin the tab to the other portion of the diaper.

The intended user manipulation of the diaper-mounted tab shown in FIG. 3 is illustrated in FIGS. 4–6. To initially fasten the tab the user peels back one half-tab part, say the part 31, of the second length portion 16 of the first or principal substrate 10, together with the corresponding pat of the first substrate adhesive 20, from the release means 26 and applies the same to another portion D2 of the diaper, as shown in FIG. 4. At this point, the other half-tab part 32 remains wrapped around the diaper portion D1. To now intially unfasten the diaper, the user removes the half-tab portion 31 from the diaper portion D2 by peeling it away as shown in FIG. 5, whereupon the diaper may be opened. At this point, the other half-tab part 32 still remains wrapped around the diaper portion D1. To now refasten the diaper, the user peels back the half-tab part 32, together with the corresponding part of the first substrate adhesive 20, from the release means 26 and applies the same to the other portion D2 of the diaper, as shown in FIG. 6.

It will thus be seen that a Y-configuration tab has been provided that is refastenable but that can be manufactured virtually as simply as prior art Y-configuration tabs that are not refastenable.

It should be evident that this disclosure is by way of example and that various changes may be made by adding, modifying or eliminating details without departing from the fair scope of the teaching contained in this disclosure. The invention is therefore not limited to particular details of this disclosure except to the extent that the following claims are necessarily so limited.

What is claimed is:

1. A refastenable tab of Y-configuration for diapers and the like formed of diaper tab stock comprising a web construction made up of initially flat but flexible substrate material and suitable to be formed in long passes along the machine direction of a coating and laminating line and to be rolled up for storage and shipment, and unrolled for use by diaper manufacturers, and fabricatable for storage and shipment completely by web coating and web-to-web laminating operations and without the necessity for folding or machine direction slitting operations, and suitable for high speed dispensing or automatic equipment, said tab including a first substrate extending, transversely to machine direction, along first and second length portions and bearing first substrate adhesive on its underside at both said first and second length portions, a second substrate extending along said first and second length portions and bearing second substrate adhesive on its underside at both said first and second length portions, release means for said first substrate adhesive located on said second substrate and below the first substrate adhesive at said second length portion, said first length portion being substantially free of said release means whereby said first substrate remains permanently associated with said second substrate throughout said first length portion up unto the border thereof that is adjacent said second length portion, said tab having two lateral sides formed by spaced transverse cuts across the machine direction of said tab stock, said tab also having an intermediate cut within the tab body, said intermediate cut extending generally intermediate said two lateral sides, and generally parallel thereto, said intermediate cut extending at least through said second length portion of said first substrate to define two side-by-side half-tab parts of said second length portions of said first substrate, each of a width to grip independently in a Y-configuration grip and each having its own part of said release means with said intermediate cut dividing said release means from itself to enable independent sequential deployment of said half-tab parts to sequentially form a first Y-configuration joint and a second Y-configuration joint.

2. A diaper having a diaper tab as defined in claim 1 applied to a first part of the diaper, the tab being applied to one edge of the diaper with the first length portions of the second substrate adhesive, second substrate, first substrate adhesive, and first substrate respectively layered on one side of said one diaper edge and with the second length portions of the second substrate adhesive and second substrate, the release means, the second length portions of the first substrate adhesive and first substrate respectively layered on the opposite side of said one diaper edge and with the borders of said first and second length portions located outboard ot such diaper edge, whereby the tab, mounted on said one edge of the diaper, may be manipulated by a person to fasten, unfasten, and refasten the diaper by (1) peeling back one half-tab part of the second length portion of the first substrate, together with the corresponding part of the second length portion of the first substrate adhesive, from the release means to deploy the same and applying the same to another part of the diaper to thereby fasten the diaper with the first and second substrates remaining joined on said one side of said diaper edge and up unto said border to establish a first Y-configuration joint for said one half-tab while allowing the remaining undeployed half-tab, including portions thereof adjacent said diaper edge, to accommodate the formation of said first Y-configuration joint and remain in suitable condition for subsequent deployment to establish a second Y-configuration joint, (2) then removing said one half-tab part from said other part of the diaper to thereby unfasten the diaper, and (3) then peeling back the other half-tab part of the second length portion of the first substrate, together with the corresponding part of the second length portion of the first substrate adhesive, from the release means to deploy the same and applying the same to said another part of the diaper to thereby refasten the diaper.

* * * * *